(12) United States Patent
Hilmersson

(10) Patent No.: US 10,426,404 B2
(45) Date of Patent: Oct. 1, 2019

(54) SENSOR JACKET

(75) Inventor: Mats Hilmersson, Bromma (SE)

(73) Assignee: ST. JUDE MEDICAL COORDINATION CENTER BVBA, Zaventem (BE)

(*) Notice: Subject to any disclaimer, the term of this patent is extended or adjusted under 35 U.S.C. 154(b) by 0 days.

(21) Appl. No.: 13/806,380

(22) PCT Filed: Jun. 16, 2011

(86) PCT No.: PCT/EP2011/060008
§ 371 (c)(1),
(2), (4) Date: Dec. 21, 2012

(87) PCT Pub. No.: WO2012/000798
PCT Pub. Date: Jan. 5, 2012

(65) Prior Publication Data
US 2013/0102927 A1    Apr. 25, 2013

Related U.S. Application Data

(60) Provisional application No. 61/359,954, filed on Jun. 30, 2010.

(30) Foreign Application Priority Data

Jun. 30, 2010    (SE) ...................................... 1050717

(51) Int. Cl.
*A61B 5/0215*    (2006.01)
*A61M 25/00*    (2006.01)
*A61B 5/00*    (2006.01)

(52) U.S. Cl.
CPC .......... *A61B 5/6851* (2013.01); *A61B 5/0215* (2013.01); *A61B 5/02152* (2013.01);
(Continued)

(58) Field of Classification Search
CPC .............. A61B 5/6851; A61B 5/02158; A61B 5/0215–02158; A61M 2025/0002;
(Continued)

(56) References Cited

U.S. PATENT DOCUMENTS 3,521,620 A * 7/1970 Cook ........................... 600/585
4,456,013 A * 6/1984 De Rossi ........... A61B 5/02156
600/488

(Continued)

FOREIGN PATENT DOCUMENTS

DE    24 20 610 A1    10/1975
EP    0 387 453 A1    9/1990
(Continued)

OTHER PUBLICATIONS tube. Dictionary.com. Dictionary.com Unabridged. Random House, Inc. <http://dictionary.reference.com/browse/tube> (accessed: Sep. 5, 2014).*

(Continued)

*Primary Examiner* — David J. McCrosky
(74) *Attorney, Agent, or Firm* — Foley & Lardner LLP

(57) ABSTRACT

A sensor guide wire includes a sensor element arranged in a jacket in a sensor region of the sensor guide wire; a core wire extending at least partly along a length of the sensor guide wire; and at least one electrical lead connected to the sensor element. The jacket is tubular and includes proximal and distal end openings, a jacket wall, a first opening arranged in the jacket wall, and a second opening arranged in the jacket wall, the first and second openings being proximate to the sensor element. The core wire is adapted to extend through the jacket via the proximal and distal end openings. At least a portion of the first opening and at least a portion of the second opening are both located in the same cross-section of (Continued)

the sensor guide wire, the cross-section being perpendicular to the longitudinal axis of the sensor guide wire.

9 Claims, 4 Drawing Sheets

(52) U.S. Cl.
CPC ............. *A61M 2025/0002* (2013.01); *A61M 2025/0003* (2013.01)

(58) Field of Classification Search
CPC ........ A61M 2025/09175; A61M 25/09; A61M 2025/0003
USPC ........ 600/462, 465, 486, 488, 505, 549, 561
See application file for complete search history.

(56) References Cited

U.S. PATENT DOCUMENTS

| | | | |
|---|---|---|---|
| 4,712,566 | A | 12/1987 | Hok |
| 4,941,473 | A | 7/1990 | Tenerz et al. |
| 5,018,529 | A | 5/1991 | Tenerz et al. |
| 5,085,223 | A | 2/1992 | Lars et al. |
| 5,125,058 | A | 6/1992 | Tenerz et al. |
| 5,437,288 | A | 8/1995 | Schwartz et al. |
| 5,549,109 | A * | 8/1996 | Samson et al. ............... 600/585 |
| RE35,648 | E | 11/1997 | Tenerz et al. |
| 5,993,378 | A * | 11/1999 | Lemelson ........... A61B 5/02154 600/109 |
| 6,019,728 | A | 2/2000 | Iwata et al. |
| 6,045,734 | A * | 4/2000 | Luther ............... A61M 25/0012 264/103 |
| 6,162,182 | A | 12/2000 | Cole |
| 6,167,763 | B1 | 1/2001 | Tenerz et al. |
| 6,248,083 | B1 | 6/2001 | Smith et al. |
| 6,295,990 | B1 * | 10/2001 | Lewis ..................... A61B 17/22 128/898 |
| 6,491,712 | B1 * | 12/2002 | O'Connor ........ A61B 17/12109 606/200 |
| 7,011,636 | B2 * | 3/2006 | Tenerz ................. A61B 5/0215 600/585 |
| 7,222,539 | B2 | 5/2007 | Tulkki |
| RE39,863 | E | 10/2007 | Smith |
| 7,724,148 | B2 | 5/2010 | Samuelsson et al. |
| 8,174,395 | B2 | 5/2012 | Samuelsson et al. |
| 8,461,997 | B2 | 6/2013 | Samuelsson et al. |
| 8,551,022 | B2 * | 10/2013 | Von Malmborg ............ 600/585 |
| 9,144,664 | B2 * | 9/2015 | Jacobsen ................. A61B 1/05 |
| 2002/0013540 | A1 | 1/2002 | Jacobsen et al. |
| 2002/0049392 | A1 | 4/2002 | Demello |
| 2002/0077520 | A1 * | 6/2002 | Segal ................ A61M 25/0045 600/1 |
| 2002/0173785 | A1 | 11/2002 | Spear et al. |
| 2003/0009208 | A1 | 1/2003 | Snyder et al. |
| 2003/0069522 | A1 | 4/2003 | Jacobsen et al. |
| 2005/0004515 | A1 | 1/2005 | Hart et al. |
| 2005/0043670 | A1 * | 2/2005 | Rosenberg ............ A61B 5/031 604/9 |
| 2005/0187487 | A1 | 8/2005 | Azizkhan et al. |
| 2005/0268725 | A1 | 12/2005 | Tulkki |
| 2006/0004346 | A1 | 1/2006 | Begg |
| 2006/0211946 | A1 | 9/2006 | Mauge et al. |
| 2007/0088220 | A1 | 4/2007 | Stahmann |
| 2008/0200770 | A1 | 8/2008 | Hubinette |
| 2009/0020961 | A1 | 1/2009 | Kameyama et al. |
| 2009/0062602 | A1 | 3/2009 | Rosenberg et al. |
| 2009/0177185 | A1 | 7/2009 | Northrop |
| 2010/0063479 | A1 | 3/2010 | Merdan et al. |
| 2010/0145308 | A1 | 6/2010 | Layman et al. |
| 2010/0152663 | A1 | 6/2010 | Darr |
| 2010/0217304 | A1 * | 8/2010 | Angel ................. A61F 2/013 606/200 |
| 2010/0228112 | A1 | 9/2010 | Von Malmborg |
| 2010/0262041 | A1 | 10/2010 | Von Malmborg |
| 2011/0004198 | A1 * | 1/2011 | Hoch ................ A61B 5/02152 604/523 |
| 2011/0160648 | A1 * | 6/2011 | Hoey .................... A61B 18/04 604/26 |
| 2011/0160680 | A1 | 6/2011 | Cage et al. |
| 2011/0213220 | A1 | 9/2011 | Samuelsson et al. |
| 2011/0245808 | A1 | 10/2011 | Voeller et al. |
| 2012/0289808 | A1 | 11/2012 | Hubinette |
| 2013/0102928 | A1 | 4/2013 | Sotos et al. |
| 2013/0274618 | A1 | 10/2013 | Hou et al. |
| 2013/0296718 | A1 | 11/2013 | Ranganathan et al. |
| 2014/0058338 | A1 | 2/2014 | Adams et al. |
| 2016/0262698 | A1 | 9/2016 | Mahlin |

FOREIGN PATENT DOCUMENTS

| | | |
|---|---|---|
| EP | 0 521 595 B1 | 5/1999 |
| EP | 1 340 516 A1 | 9/2003 |
| EP | 0 877 574 B1 | 10/2003 |
| EP | 1 849 409 A1 | 10/2007 |
| EP | 2 085 108 A2 | 8/2009 |
| EP | 1 545 680 B1 | 9/2010 |
| SE | 441725 B | 11/1985 |
| SE | 453561 B | 2/1988 |
| SE | 454045 B | 3/1988 |
| SE | 460396 B | 10/1989 |
| SE | 469454 B | 7/1993 |
| WO | WO-97/00641 A1 | 1/1997 |
| WO | WO-00/69323 A2 | 11/2000 |
| WO | WO 03/094693 A2 | 11/2003 |
| WO | WO-2004/011076 A2 | 2/2004 |
| WO | WO-2007/050718 A1 | 5/2007 |
| WO | WO-2009/020954 A1 | 2/2009 |
| WO | WO-2009/029639 A1 | 3/2009 |
| WO | WO 2009/054803 A1 | 4/2009 |
| WO | WO-2009/112060 A1 | 9/2009 |
| WO | WO-2011/041720 A2 | 4/2011 |
| WO | WO-2012/000798 A1 | 1/2012 |
| WO | WO-2016/138226 A1 | 9/2016 |

OTHER PUBLICATIONS

"In", The American Heritage Dictionary of the English Language, Fifth Edition (2014), Houghton Mifflin Harcourt Publishing Company. pp. 1-3. Retrieved from <https://www.ahdictionary.com/word/search.html?q=IN> on Mar. 25, 2015.*
"-Like". 2011. In the American Heritage Dictionary of the English Language, Boston: Houghton Mifflin. <http://search.credoreference.com/content/entry/hmdictenglang/like/0>.*
Machine Translation of DE 2420610.*
International Preliminary Report on Patentability, PCT/IB2013/000903, dated Nov. 13, 2014, 11 pages.
USPTO Office Action, U.S. Appl. No. 13/804,342, dated Jan. 16, 2015, 9 pages.
USPTO Office Action, U.S. Appl. No. 13/804,342, dated Sep. 12, 2014, 18 pages.
USPTO Office Action, U.S. Appl. No. 13/804.342, dated Nov. 19, 2015, 12 pages.
USPTO Office Action, U.S. Appl. No. 13/804,342, dated Apr. 7, 2016, 13 pages.
PCT/ISA/206, International Application No. PCT/US2016/019498, 7 pages.
Radi Medical Systems AB, PressureWire Certus, Brochure, 60680 Rev. 03, Apr. 2008.
U.S. Appl. No. 15/053,308, filed Feb. 25, 2016, St. Jude Medical Coordination Center BVBA.
European Office Action, Application No. 13 723 953.9, dated Jun. 27, 2017, 6 pages.
International Search Report and Written Opinion, PCT/US2016/019498, dated Jul. 4, 2016, 17 pages.
International Preliminary Report on Patentability, PCT/US2016/019498, dated Sep. 8, 2017, 11 pages.
USPTO Notice of Allowance, U.S. Appl. No. 13/804,342 dated Sep. 5, 2017, 7 pages.
European Office Action, dated Jul. 20, 2018, 6 pages.

(56) References Cited

OTHER PUBLICATIONS

Japanese Office Action and English translation, Application No. 2016-525613, dated Dec. 5, 2017, 6 pages.
USPTO Notice of Allowance, U.S. Appl. No. 13/804,342, dated May 10, 2018, 8 pages.
Japanese Office Action and English translation, Application No. 2016-525613, dated Mar. 21, 2017, 14 pages.
USPTO Notice of Allowance, U.S. Appl. No. 13/804,342, dated Oct. 18, 2018, 7 pages.
USPTO Office Action, U.S. Appl. No. 15/030,770, dated Oct. 18, 2018, 14 pages.
European Extended Search Report, dated Nov. 19, 2018, 6 pages.
International Search Report and Written Opinion, PCT/US2019/024292, dated Jun. 26, 2019, 11 pages.
USPTO Notice of Allowance, U.S. Appl. No. 15/030,770, dated Jul. 8, 2019, 9 pages.

\* cited by examiner

SENSOR JACKET

FIELD OF THE INVENTION

The present invention relates generally to sensor and guide wire assemblies, in which a sensor element is mounted at the distal end of a guide wire for intravascular measurements of physiological variables in a living body, and particularly to the mounting arrangement of the sensor element, and more particularly to a jacket in which the sensor element is disposed, according to the preamble of the independent claim.

BACKGROUND OF THE INVENTION

In many medical procedures, various physiological conditions present within a body cavity need to be monitored. These physiological conditions are typically physical in nature—such as pressure, temperature, rate-of-fluid flow, and provide the physician or medical technician with critical information as to the status of a patient's condition.

One device that is widely used to monitor conditions is the blood pressure sensor. A blood pressure sensor senses the magnitude of a patient's blood pressure, and converts it into a representative electrical signal that is transmitted to the exterior of the patient.

For most applications it is required that the sensor is electrically energized. Some means of signal and energy transmission is thus required, and most commonly extremely thin electrical cables, sometimes called microcables, are provided inside a guide wire, which itself is provided in the form of a tube, which often has an outer diameter in the order of 0.35 mm, and oftentimes is made of steel.

In order to increase the bending strength of the tubular guide wire, a core wire is positioned inside the tube. The core wire also helps to improve "pushability" and "torquability" of the guide wire. The mentioned electrical cables are e.g. positioned in the space between the inner lumen wall and the core wire.

Sensor and guide wire assemblies in which a sensor is mounted at the distal end of a guide wire are known. In U.S. Pat. No. Re. 35,648, which is assigned to the present assignee, an example of such a sensor and guide wire assembly is disclosed, where a sensor guide comprises a sensor element, an electronic unit, a signal transmitting cable connecting the sensor element to the electronic unit, a flexible tube having the cable and the sensor element disposed therein, a solid metal wire, and a coil attached to the distal end of the solid wire. The sensor element comprises a pressure sensitive device, typically a membrane, with piezoresistive elements connected in a Wheatstone bridge-type of arrangement mounted thereon.

As is disclosed in, for example, U.S. Pat. No. 6,167,763, which also is assigned to the present assignee, the sensor element can be arranged inside a short tube (usually referred to as a sleeve or jacket), which protects the sensor element and comprises an aperture through which the pressure sensitive device is in contact with the ambient medium. The U.S. Pat. No. 6,167,763 further illustrates that a first coil may be attached to the distal end of the jacket and that a similar second coil may be attached to the proximal end of the jacket. The solid metal wire—which, as also mentioned above, in the art usually is referred to as the core wire—extends through the interior of the jacket and may be provided with an enlarged diameter portion adapted for mounting of the sensor element.

U.S. Pat. No. 7,222,539 discloses a jacket, wherein a sensor element and a core wire are provided in separate compartments. Another example of a sensor guide wire comprising a sensor enclosed by a sensor housing is disclosed in WO 2006/037082 A2.

In WO 03094693 A2, a pressure-measuring apparatus is disclosed, the pressure-measuring apparatus comprises a sensor transducer adapted to be incorporated in a catheter.

DE 2420610 A1, discloses a sensor for measuring pressure, the sensor is adapted to be incorporated in a catheter. The sensor is enclosed by a protecting tube.

U.S. Pat. No. 6,019,728 discloses a catheter including a catheter tube to be inserted into a body. A plurality of sensing portions are arranged in the catheter tube. Two pressure communication holes are provided in the wall of the catheter tube to communicate the ambient pressure of the tube into the interior of the tube.

In US 2007088220 A1 an implantable medical device including a physiological sensor is disclosed. The sensor is embedded in a mesh structure of a stent-like structure.

In US 20050187487 A1 and US 20060211946 A1, further examples of catheters provided with sensors are disclosed.

U.S. Pat. No. 6,162,182 discloses a cannula usable to remove blood from a patient during surgery.

Generally, a sensor and guide wire assembly comprises a sensor element in the form of an elongated, essentially rectangular chip with a pressure sensitive member in the form of a membrane provided thereon. The sensor chip is arranged inside a jacket, which besides the sensor chip also accommodates a portion of a core wire and at least one electrical lead connected to the sensor element. A first coil may be attached to the distal end of the jacket, and optionally a second coil may be attached to the proximal end of the jacket. The first and second coils may be attached to the respective end of the jacket, e.g. by gluing, or alternatively soldering.

Although sensor and guide wire assemblies comprising a jacket designed according to the techniques presented by the present assignee in practise have proven to work very well, there are continuously ongoing efforts to improve the performance and functionality of the sensor and guide wire assemblies.

According to the prior art, the jacket is provided with an aperture or window, through which the pressure sensitive part (typically a membrane) of the sensor element is in communication with a surrounding medium, e.g. blood. Now, it has—for the first time—been recognized that the dimensions of the aperture, the sensor element and the interior of the jacket in combination with the particular mounting arrangement of the sensor element are such that air present within the jacket and/or adhering to the surface of the jacket or sensor element has a tendency to be entrapped within the jacket and/or forming an air bubble covering the aperture in the jacket. In other words, the ambient fluid (e.g. blood) does not wet the sensor element and the membrane completely, which affects the signal quality of the device.

An object of the present invention is therefore to provide a sensor and guide wire assembly comprising an improved jacket, with which the above-mentioned wetting problem is eliminated or at least minimized.

SUMMARY OF THE INVENTION

By providing a jacket with multiple holes an improved wetting can be achieved, which ensures a more reliable and stable sensor output.

The sensor guide wire for intravascular measurements of at least one physiological, or other, variable in a living body, in accordance with the present invention, comprises a sensor element arranged in a jacket in a sensor region of said sensor guide wire, a core wire extending at least partly along the length of said sensor guide wire, at least one electrical lead connected to said sensor element, wherein said jacket is tubular and provided with a jacket wall, and further comprises a first opening arranged in said jacket wall, said jacket is further provided with proximal and distal end openings, and wherein a core wire is adapted to extend through said jacket via said proximal and distal end openings, and wherein the sensor guide wire has an outer diameter of approximately 0.35 mm, and wherein said jacket further comprises at least a second opening arranged in said jacket wall.

SHORT DESCRIPTION OF THE APPENDED DRAWINGS

DETAILED DESCRIPTION OF PREFERRED EMBODIMENTS OF THE INVENTION

Figure 1:
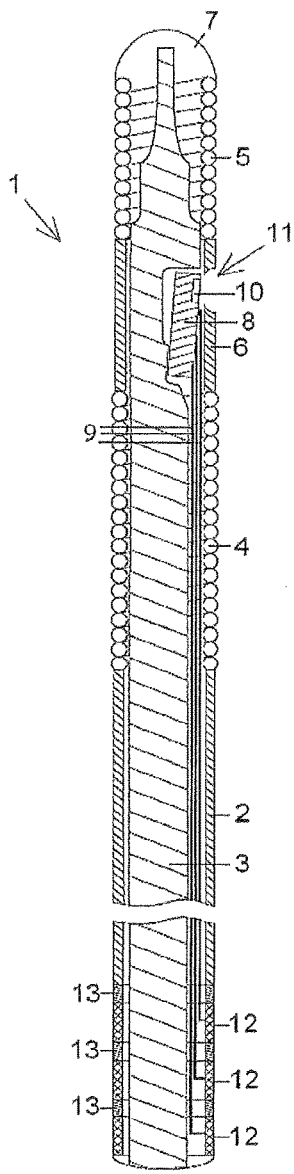
FIG. 1 illustrates schematically the general design of a sensor and guide wire assembly according to the prior art.

For better understanding of the context in which the present invention is going to be used, a sensor and guide wire assembly 1 of a conventional design is illustrated in FIG. 1. The sensor guide 1 comprises a hollow tube 2, a core wire 3, a first coil 4, a second coil 5, a jacket or sleeve 6, a dome-shaped tip 7, a sensor element or chip 8, and one or several electrical leads 9. The proximal end of the first coil 4 is attached to the distal end of the hollow tube 2, while the distal end of the first coil 4 is attached to the proximal end of the jacket 6. The proximal end of the second coil 5 is connected to the distal end of the jacket 6, and the dome-shaped tip 7 is attached to the distal end of the second coil 5. The core wire 3 is at least partly disposed inside the hollow tube 2 such that the distal portion of the core wire 3 extends out of the hollow tube 2 and into the second coil 5. The sensor element 8 is mounted on the core wire 3 at the position of the jacket 6, and is through the electrical leads 9 connected to an electronic unit (not shown in FIG. 1). The sensor element 8 comprises a pressure sensitive device in the form of a membrane 10, which through an aperture 11 in the jacket 6 is in communication with a medium, such as blood, surrounding at least the distal portion of the sensor guide 1. At the proximal end of the sensor guide 1 each electrical lead is connected to a conductive member 12 and the conductive members 12 are insulated from each other by insulating members 13, to thereby form a male connector for the sensor guide 1.

Although not shown in FIG. 1, the sensor element 8 further comprises an electrical circuitry, which in a Wheatstone bridge-type of arrangement is connected to one or several piezoresistive elements provided on the membrane 10. As is well known in the art, a certain pressure exerted on the membrane 10 from the surrounding medium will thereby correspond to a certain stretching of the membrane 10 and thereby to a certain resistance of the piezoresistive elements mounted thereon and, in turn, to a certain output from the sensor element 8.

Figure 2:
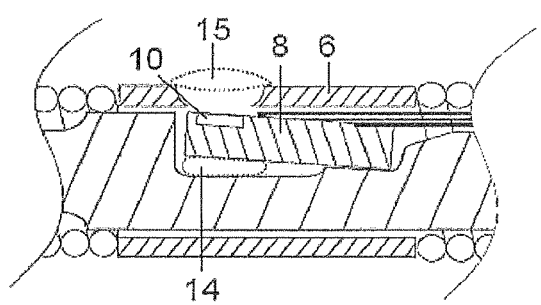
FIG. 2 shows a portion of the sensor and guide wire assembly of FIG. 1, and illustrates how air can be entrapped within a jacket and form a bubble on the surface of a jacket according to the prior art.

FIG. 2 shows the jacket portion of the sensor guide 1 of FIG. 1, and illustrates how air 14 can be entrapped within the jacket 6 or form a bubble 15 covering the aperture 11 in the jacket 6. Clearly, the air bubble 15, which covers the aperture 11, will create some undefined intermediate medium which prevents direct fluid contact between the ambient medium (typically blood) and the pressure sensitive membrane 10, and it should also be clear that if the air bubble 15, or parts thereof, disappears, the output from sensor element 8 will be affected. Air 14 entrapped within the jacket 6 exerts pressure on the sensor element 8 and can induce stress in the membrane or in the sensor element 8, whose output can change if the air 14 escapes out of the jacket 6 during use of the sensor guide 1. The above explanations of how air can affect the measurements are merely intended to be suggestive, but it should be clear that all uncontrolled factors should be eliminated in order to produce a sensor and guide wire which is as reliable as possible. Here, it can be mentioned that the standard outer diameter of a sensor guide is only 0.35 mm (0.014 inch), while an aperture in a jacket can have a diameter of about 0.25 mm.

To solve the problems outlined above, the present inventors suggest a sensor and guide wire comprising a jacket 20 with multiple openings, which allows for complete or at least improved wetting of the sensor element 18 and membrane. In contrast to the previously known jackets, which have only a first opening, through which first opening a membrane senses e.g. the surrounding pressure, and end openings, through which a core wire extends, the jacket 20 comprises further at least a second opening 23.

Figure 3:
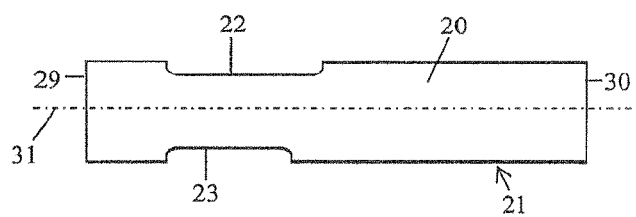
FIG. 3 illustrates a jacket according to a first embodiment of the present invention.

In FIG. 3 a first embodiment of a jacket 20 for a sensor and guide wire assembly, for intravascular measurements of at least one physiological, or other, variable in a living body, is schematically illustrated. The jacket 20 is tubular and provided with a jacket wall 21, and comprises a first opening 22 arranged in said jacket wall 21. Through this first opening 22, or at least through the first opening 22, the sensor element 18 (not shown in FIG. 3) is adapted to sense one or many physiological, or other, variables. The jacket 20 further comprises at least a second opening 23 arranged in the jacket wall 21. The second opening 23 allows the entrapped air within the jacket 20 to escape out from the jacket 20, or even prevents entrapped air to occur. A second opening 23 also provides for a better fluid communication, which prevents an air bubble from being formed over the aforementioned aperture in the jacket 20. According to this preferred embodiment the second opening 23 is arranged at the opposite side of the tubular jacket 20 in relation to said first opening 22. Further, the jacket 20 is hollow and may be provided with proximal and distal end openings (29, 30).

According to a preferred embodiment of the present invention, and as also shown in FIG. 3, the jacket 20 has a longitudinal axis 31, and the jacket wall 21 extends essentially parallel to said longitudinal axis 31. The jacket 20 may have a circular, a square, or an oval cross section in a plane perpendicular to said longitudinal axis 31.

Figure 4A:
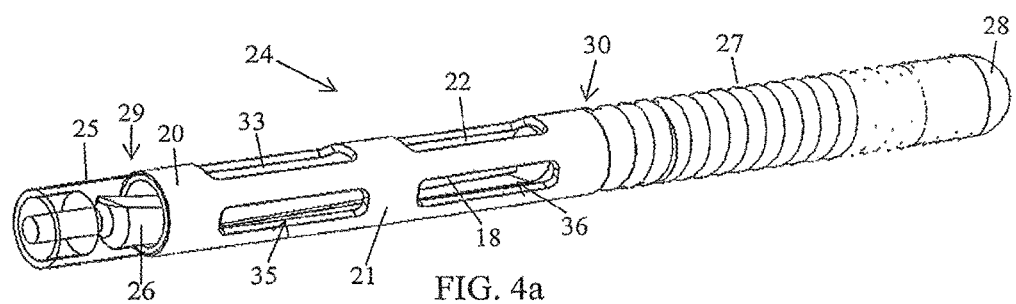
FIG. 4a illustrates a sensor guide wire and a jacket according to a second embodiment of the present invention.

In FIG. 4a, a sensor guide wire 24 and a jacket 20 according to a second embodiment of the present invention, is shown. The sensor guide wire 24 comprises a hollow tube 25, a core wire 26, at least a second coil 27, a sensor element 18 arranged in a jacket 20 in a sensor region of said sensor guide wire 24, a dome-shaped tip 28, and one or several electrical leads (not shown). As is shown in FIG. 4a, the jacket 20 is fixed relative to the core wire 26. In this embodiment, the jacket 20 is provided with a plurality of elongated openings 22, 23, 33, 34, 35, 36, 37 (23, 34, 37 not shown in FIG. 4a) distributed at the jacket wall 21 all around the jacket 20, which allows air entrapped within the jacket 20 to escape out therefrom.

Figure 4B:
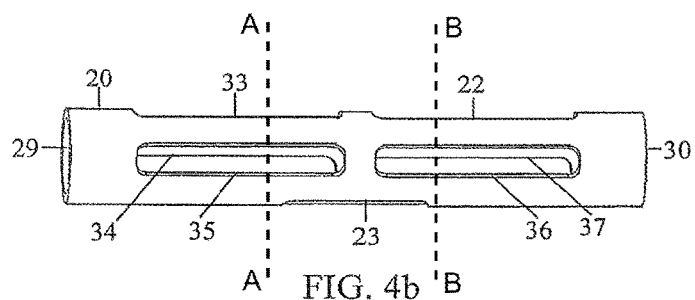
FIG. 4b illustrates the jacket according to the second embodiment, also shown in FIG. 4a, of the present invention.

FIG. 4b also illustrates the jacket 20 according to the second embodiment of the present invention. The jacket 20 has a first opening 22 and a second opening 23 arranged at the opposite side of the jacket 20 in relation to the first opening 22. In addition, the jacket 20 is provided with yet further five openings denoted 33, 34, 35, 36 and 37. Thus, according to the second embodiment of the present invention the jacket 20 is provided with seven openings 22, 23, 33, 34, 35, 36, 37 distributed at the jacket wall 21 all around the jacket 20, which are configured to allow a pressure sensitive device of the sensor element 18 to be in communication with a medium surrounding the jacket 20.

As shown in FIGS. 4a and 4b, the openings 33, 34, 35 (in this case, three openings) constitute a first set of a plurality of openings. At least a portion of the openings 33, 34, 35 in the first set are located in a same first cross-section A-A (shown in FIG. 4b) of the sensor guide wire, the first cross-section A-A being perpendicular to a longitudinal axis of the sensor guide wire 24. As also shown in FIGS. 4a and 4b, the openings 22, 36, 37 (in this case, three openings) constitute a second set of a plurality of openings. At least a portion of the openings 22, 36, 37 in the second set are located in a same second cross-section B-B (shown in FIG. 4b), the second cross-section B-B being perpendicular to a longitudinal axis of the sensor guide wire 24. The first set of openings 33, 34, 35 extending through the jacket wall includes a first opening 33 located above the sensor element, a second opening 34 located at a first lateral side of the sensor element, and a third opening 35 located at a second lateral side of the sensor element. The first, second, and third openings 33, 34, 35 are elongated in a longitudinal direction of the jacket 20, and are aligned in a circumferential direction of the jacket 20. The second set of openings 22, 36, 37 include a fourth opening 22 that is aligned with the first opening 33 in a longitudinal direction of the jacket 20, a fifth opening 37 that is aligned with the second opening 34 in the longitudinal direction of the jacket, and a sixth opening 36 that is aligned with the third opening 35 in the longitudinal direction of the jacket. The fourth, fifth, and sixth openings 22, 36, 37 are elongated in the longitudinal direction of the jacket 20. The jacket also includes a seventh opening, which is the opening 23.

Figure 5:
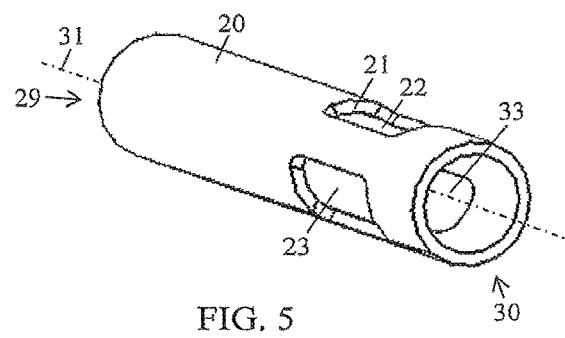
FIG. 5 shows a jacket according to a third embodiment of the present invention.

In FIG. 5 the jacket 20 according to a third embodiment of the present invention, is illustrated. The jacket 20 has exactly three openings that are aligned in the circumferential direction of the jacket 20: a first opening 22, a second opening 23 and a third opening 33. As shown in FIG. 5, first opening 22 is to be located above the sensor element, the second opening 23 is to be located at a first lateral side of the sensor element, and the third opening 33 is to be located at a second lateral side of the sensor element. The jacket 20 has a circular cross section in a plane perpendicular to the longitudinal axis 31 and the openings 22, 23, 33 are arranged evenly distributed around said jacket wall 21.

Figure 6:
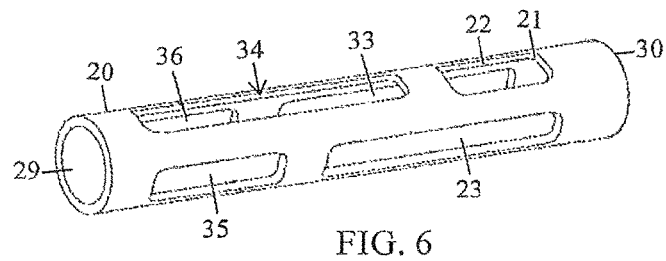
FIG. 6 shows a jacket according to a fourth embodiment of the present invention.

FIG. 6 shows the jacket 20 according to a fourth embodiment of to the present invention. According to this embodiment, the jacket 20 has a first 22 and a second 23 opening and is further provided with proximal and distal end openings 29, 30. Furthermore, the jacket 20 is provided with yet further a plurality of elongated openings 33, 34, 35, 36, the openings 33, 34, 35, 36 having different sizes in relation to each other.

Figure 7A:
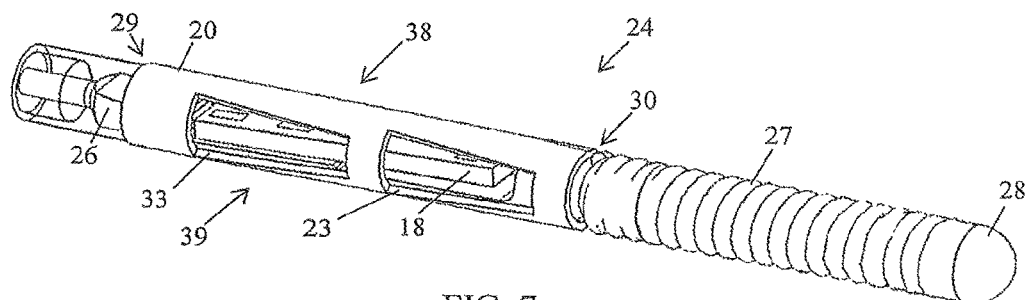
FIG. 7a shows a sensor guide wire and a jacket according to a fifth embodiment of the present invention.
Figure 7B:
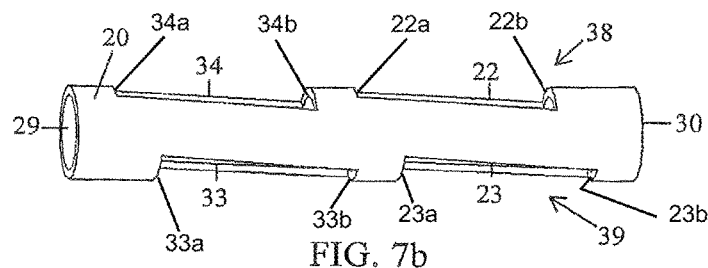
FIG. 7b illustrates the jacket from above according to the fifth embodiment, also shown in FIG. 7a, of the present invention.

FIG. 7a shows the sensor guide wire 24 and the jacket 20 according to a fifth preferred embodiment of the present invention. The jacket 20 is provided with proximal and distal end openings 29, 30 and a core wire 26 extends through said jacket 20 via the proximal and distal end openings 29, 30. Further, the jacket 20 is provided with a first 22, a second 23, a third 33, and a fourth opening 34, which openings are arranged in pairs on opposite sides of the jacket 20. According to this preferred embodiment, the openings 22, 23, 33, 34 are asymmetrical. The first and the fourth openings 22, 34 (not shown in FIG. 7a), arranged on a first side 38 of the jacket 20, are wider in a distal part than in a proximal part of the openings 22, 34. Whereas the second and the third openings 23, 33, arranged on a second side 39, opposite to the first side 38 of the jacket 20, are wider in a proximal part than in a distal part of the openings 23, 33. In other words, as shown in FIG. 7b, distal edges 22b, 34b of the openings 22, 34, which extend in a substantially circumferential direction around the jacket 20, are longer than proximal edges 22a, 34a of the openings 22, 34, which also extend in a substantially circumferential direction around the jacket 20. And, as also shown in FIG. 7b, proximal edges 23a, 33a of the openings 23, 33, which extend in a substantially circumferential direction around the jacket 20, are longer than distal edges 23b, 33b of the openings 23, 33, which also extend in a substantially circumferential direction about the jacket 20. The openings 22, 23, 33, 34 are configured to allow a pressure sensitive device of the sensor element 18 to be in communication with a medium surrounding the jacket 20. An advantage of the openings of the two pairs being wider in different parts (distally or proximally) at different sides, is that it is not possible to arrange the jacket 20 in an incorrect direction when assembling the jacket 20 and the sensor guide wire 24. Thus, the openings at for example the first side 38 will be arranged in the same way independent of which one of the end openings 29, 30 of the jacket 20 is being arranged e.g. distally. Another advantage of this embodiment is that, the fluid used for flushing the sensor guide wire comprising the jacket 20 before insertion of the sensor guide wire, in greater extent stays inside the jacket 20 when flushed right through the jacket 20.

FIG. 7b illustrates the jacket 20 from above according to the fifth embodiment of the present invention. FIG. 7b illustrates that the two pairs of openings 22, 23, 33, 34 are arranged on opposite sides 38, 39 of the jacket 20.

According to another embodiment of the present invention, the openings 22, 23, 33, 34 arranged in pairs on opposite sides of the jacket 20 may be slightly displaced in relation to each other along the longitudinal axis 31.

Figure 8:
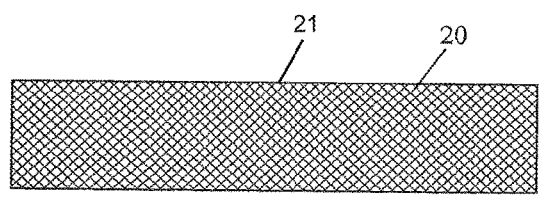
FIG. 8 shows a jacket according to a sixth embodiment of the present invention.

In FIG. 8 the jacket 20 according to a sixth embodiment of the present invention, is illustrated. According to this embodiment, the jacket wall 21 is mesh-like, and thus provided with a plurality of openings evenly distributed at said jacket wall 21. In other words, in this embodiment, the jacket 20 is a mesh jacket 20 having a jacket wall 21 with a plurality of evenly distributed openings of substantially the same size and shape, as is shown in FIG. 8. The evenly distributed openings are configured to allow a pressure sensitive device of the sensor element 18 to be in communication with a medium surrounding the jacket 20.

Figure 9:
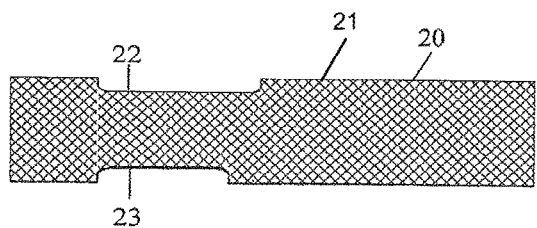
FIG. 9 shows a jacket according to a seventh embodiment of the present invention.
Figure 10:
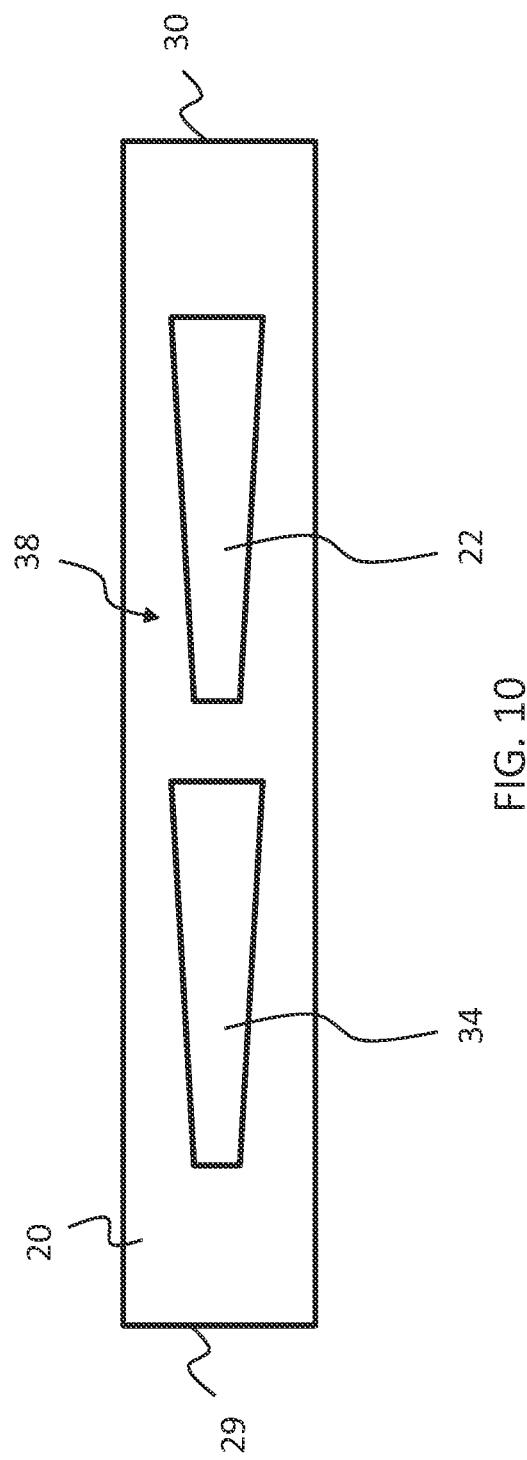
FIG. 10 is a schematic view of a jacket that includes openings that are wider in their distal parts than in their proximal parts.

FIG. 9 shows the jacket 20 according to a seventh embodiment of the present invention. In this embodiment the jacket wall 21 is mesh-like, and further the jacket 20 is provided with a first 22 and a second opening 23. The second opening 23 is arranged at the opposite side of the tubular jacket 20 in relation to said first opening 22. The jacket 20 is hollow and may be provided with proximal and distal end openings 29, 30. In other words, the jacket 20 is a mesh jacket 20 having a jacket wall 21 with a plurality of evenly distributed openings of substantially the same size and shape, and further including a first opening 22 and a second opening 23, wherein the first and second openings 22, 23 are larger than the evenly distributed openings in the jacket wall 21, as is shown in FIG. 9. The evenly distributed openings and the first and second openings 22, 23 are configured to allow a pressure sensitive device of the sensor element 18 to be in communication with a medium surrounding the jacket 20.

It should be noted that previous embodiments are applicable, regarding the number of openings and how they are arranged, in a jacket provided with a mesh-like wall.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A sensor guide wire for intravascular measurement of a physiological variable, comprising:
    a core wire extending at least partly along a length of the sensor guide wire;
    a sensor element mounted on the core wire, in a sensor region of the sensor guide wire, the sensor element comprising a pressure sensitive device;
    a jacket having a jacket wall, the jacket being fixed relative to the core wire; and
    at least one lead connected to the sensor element;
    wherein the jacket is tubular and includes a proximal end opening, a distal end opening, and a first set of openings extending through the jacket wall,
    wherein the core wire extends through the jacket via the proximal and distal end openings, and
    wherein the first set of openings extending through the jacket wall includes a first opening located above the sensor element, a second opening located at a first lateral side of the sensor element, and a third opening located at a second lateral side of the sensor element, and wherein the first, second, and third openings are elongated in a longitudinal direction of the jacket, and are aligned in a circumferential direction of the jacket.

2. The sensor guide wire according to claim 1, wherein the jacket further includes a second set of openings extending through the jacket wall, the second set of openings including a fourth opening that is aligned with the first opening in a longitudinal direction of the jacket, a fifth opening that is aligned with the second opening in the longitudinal direction of the jacket, and a sixth opening that is aligned with the third opening in the longitudinal direction of the jacket, wherein the fourth, fifth, and sixth openings are elongated in the longitudinal direction of the jacket.

3. The sensor guide wire according to claim 2, wherein the jacket further includes a seventh opening.

4. The sensor guide wire according to claim 2, wherein the first set of openings is located at a distal portion of the jacket, and the second set of openings is located at a proximal portion of the jacket.

5. The sensor guide wire according to claim 1, wherein the jacket wall extends essentially parallel to a longitudinal axis of the sensor guide wire.

6. The sensor guide wire according to claim 1, wherein the first set of openings includes exactly three openings that are aligned in the circumferential direction of the jacket: the first opening, the second opening, and the third opening.

7. The sensor guide wire according to claim 1, wherein the pressure sensitive device is a membrane.

8. The sensor guide wire according to claim 7, wherein the sensor element further comprises one or more piezoresistive elements provided on the membrane.

9. The sensor guide wire according to claim 1, wherein the first set of openings is located at a distal portion of the jacket.

* * * * *